United States Patent [19]

Sih

[11] 4,278,813

[45] Jul. 14, 1981

[54] 19,20-DIDEHYDRO-13,14-DIHYDRO-PG$_2$, SULFONYL AMIDES

[75] Inventor: John C. Sih, Kalamazoo, Mich.

[73] Assignee: The Upjohn Company, Kalamazoo, Mich.

[21] Appl. No.: 85,742

[22] Filed: Oct. 17, 1979

Related U.S. Application Data

[62] Division of Ser. No. 26,066, Apr. 2, 1979.

[51] Int. Cl.$^3$ .................... A61K 31/18; C07C 143/75
[52] U.S. Cl. ........................................ 564/98; 424/321
[58] Field of Search .................. 260/556 AC; 564/98, 564/99

[56] References Cited

U.S. PATENT DOCUMENTS

| | | | |
|---|---|---|---|
| 3,919,285 | 11/1975 | Axen | 260/408 X |
| 3,954,741 | 5/1976 | Schaaf et al. | 542/416 |
| 4,064,351 | 12/1977 | Sakai et al. | 560/121 |
| 4,098,805 | 7/1978 | Bundy | 260/556 AC X |
| 4,152,527 | 5/1979 | Hess et al. | 260/556 AC X |
| 4,169,895 | 10/1979 | Hess et al. | 260/556 AC X |

OTHER PUBLICATIONS

CA 88:190218 (1978).

*Primary Examiner*—Thomas A. Waltz
*Attorney, Agent, or Firm*—Robert A. Armitage

[57] ABSTRACT

The present invention provides novel 19,20-didehydro-13,14-dihydro-PG$_2$, sulfonyl amides, methods for their preparation and pharmacological use for the induction of prostaglandin-like effect.

1 Claim, No Drawings

19,20-DIDEHYDRO-13,14-DIHYDRO-PG$_2$, SULFONYL AMIDES

CROSS REFERENCE TO RELATED APPLICATIONS

The present application is a division of Ser. No. 026,066, filed Apr. 2, 1979, pending issuance as a U.S. patent.

BACKGROUND OF THE INVENTION

The present invention relates to novel prostaglandin analogs. Particularly, these compounds are analogs of the prostaglandins wherein the C-20-C-19 position is unsaturated, i.e., 19,20-didehydro-PG compounds. Most particularly, the present invention relates to novel 19,20-didehydro-13,14-dihydro-PG$_2$, sulfonyl amides, a disclosure of the preparation and use of which is incorporated here by reference from U.S. Pat. No. 4,228,604.

PRIOR ART

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 026,066.

SUMMARY OF THE INVENTION

The present invention particularly provides:
A compound of the formula

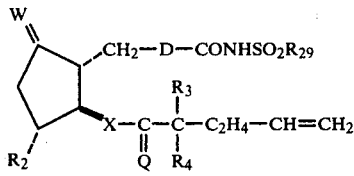

wherein D is
(1) cis—CH=CH—CH$_2$—(CH$_2$)$_g$—CH$_2$—,
(2) cis—CH=CH—CH$_2$-(CH$_2$)$_g$—CF$_2$—,
(3) cis—CH$_2$—CH=CH—CH$_2$—CH$_2$—,
(4) trans—(CH$_2$)$_3$—CH=CH—,
wherein Q is

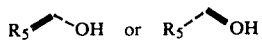

wherein R$_5$ is hydrogen or methyl, R$_{29}$ is
alkyl of one to 4 carbon atoms, inclusive, wherein R$_2$ is hydrogen, hydroxyl, or hydroxymethyl; wherein R$_3$ and R$_4$ are hydrogen, methyl, or fluoro, being the same or different, with the proviso that one of R$_3$ and R$_4$ is fluoro only when the other is hydrogen or fluoro;
wherein W is

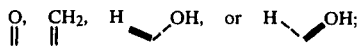

and wherein X is —CH$_2$CH$_2$—.

The compounds of the present invention are particularly useful for inducing prostaglandin-like biological effects, as is described in U.S. Ser. No. 026,066. Uses of compounds in accordance with the present invention include, therefore, anti-asthmatic indication.

I claim:
1. A compound of the formula

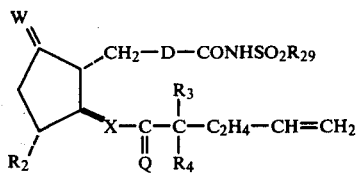

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
wherein Q is

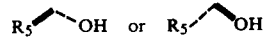

wherein R$_5$ is hydrogen or methyl, R$_{29}$ is
alkyl of one to 4 carbon atoms, inclusive, wherein R$_2$ is hydrogen, hydroxyl, or hydroxymethyl; wherein R$_3$ and R$_4$ are hydrogen, methyl, or fluoro, being the same or different, with the proviso that one of R$_3$ and R$_4$ is fluoro only when the other is hydrogen or fluoro;
wherein W is

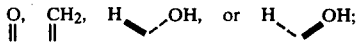

and wherein X is —CH$_2$CH$_2$—.

* * * * *

UNITED STATES PATENT OFFICE
CERTIFICATE OF CORRECTION

Patent No. 4,278,813      Dated 14 July 1981

Inventor(s) John C. Sih

It is certified that error appears in the above-identified patent and that said Letters Patent are hereby corrected as shown below:

Column 1, lines 8-9, "pending issuance as a U.S. Patent" should read -- now U.S. Patent 4,243,611 --; line 20, "U.S. Pat. No. 4,228,604" should read -- U.S. Pat. No. 4,228,104 --;

Column 2, line 15, "U.S. Ser. No. 026,066" should read -- U.S. Patent 4,243,611 --.

Signed and Sealed this

Tenth Day of November 1981

[SEAL]

*Attest:*

*Attesting Officer*

GERALD J. MOSSINGHOFF

*Commissioner of Patents and Trademarks*